United States Patent
Yaacobi

(10) Patent No.: US 7,094,226 B2
(45) Date of Patent: Aug. 22, 2006

(54) OPHTHALMIC DRUG DELIVERY DEVICE

(75) Inventor: Yoseph Yaacobi, Forth Worth, TX (US)

(73) Assignee: Alcon, Inc., Hunenberg (CH)

( * ) Notice: Subject to any disclaimer, the term of this patent is extended or adjusted under 35 U.S.C. 154(b) by 523 days.

(21) Appl. No.: 10/706,105

(22) Filed: Nov. 12, 2003

(65) Prior Publication Data

US 2004/0106906 A1      Jun. 3, 2004

Related U.S. Application Data

(63) Continuation of application No. PCT/US02/23048, filed on Jul. 22, 2002.

(60) Provisional application No. 60/307,284, filed on Jul. 23, 2001.

(51) Int. Cl.
*A61M 35/00*     (2006.01)

(52) U.S. Cl. ............... 604/294; 604/289; 604/301; 604/521

(58) Field of Classification Search ........ 604/289–301, 604/506, 513, 521, 890.1, 891.1, 892.1, 93.01
See application file for complete search history.

(56) References Cited

U.S. PATENT DOCUMENTS

| | | | |
|---|---|---|---|
| 3,416,530 A | 12/1968 | Ness | |
| 3,828,777 A | 8/1974 | Ness | |
| 3,884,232 A * | 5/1975 | Braun | 132/333 |
| 4,014,335 A | 3/1977 | Arnold | |
| 4,256,108 A | 3/1981 | Theeuwes | |
| 4,300,557 A | 11/1981 | Refojo et al. | |
| 4,327,725 A | 5/1982 | Cortese et al. | |
| 4,624,848 A | 11/1986 | Lee | |
| 4,853,224 A | 8/1989 | Wong | |
| 4,946,450 A | 8/1990 | Erwin | |
| 4,997,652 A | 3/1991 | Wong | |
| 5,030,214 A * | 7/1991 | Spector | 604/301 |
| 5,147,647 A | 9/1992 | Darougar | |
| 5,164,188 A | 11/1992 | Wong | |
| 5,178,635 A | 1/1993 | Gwon et al. | |
| 5,300,114 A | 4/1994 | Gwon et al. | |

(Continued)

FOREIGN PATENT DOCUMENTS

DE        40 22 553        1/1992

(Continued)

OTHER PUBLICATIONS

"Bausch & Lomb and Control Delivery Systems Agree to Develop Breakthrough Therapeutic Products for Severe Eye Diseases;" Business Wire via First!; NewsEdge Corp.; Jun. 15, 1999; 4 pp.

(Continued)

*Primary Examiner*—Kevin Sirmons
*Assistant Examiner*—Jaime Corrigan
(74) *Attorney, Agent, or Firm*—W. David Lee

(57) ABSTRACT

An ophthalmic drug delivery device having a first end and a second end, an injection port, a reservoir, and a sleeve is disclosed. The injection port is for sealingly engaging a needle of a syringe, which is for providing a fluid comprising a pharmaceutically active agent. The reservoir is disposed within the device, is fluidly coupled to the injection port, and has an opening for communicating the fluid to an outer surface of a sclera of an eye. The sleeve is for engaging the device proximate overlapping portions of the first end and the second end for forming a generally ring-shaped three-dimensional geometry upon implantation of the device on the outer surface of the sclera. The device is useful for the treatment of a disease of the posterior segment of the eye.

7 Claims, 4 Drawing Sheets

U.S. PATENT DOCUMENTS

| | | |
|---|---|---|
| 5,322,691 A | 6/1994 | Darougar et al. |
| 5,378,475 A | 1/1995 | Smith et al. |
| 5,403,901 A | 4/1995 | Namdaran et al. |
| 5,443,505 A | 8/1995 | Wong et al. |
| 5,466,233 A | 11/1995 | Weiner et al. |
| 5,466,466 A | 11/1995 | Muller |
| 5,476,511 A | 12/1995 | Gwon et al. |
| 5,516,522 A | 5/1996 | Peyman et al. |
| 5,632,984 A | 5/1997 | Wong et al. |
| 5,679,666 A | 10/1997 | Clark |
| 5,710,165 A | 1/1998 | Kapin et al. |
| 5,725,493 A | 3/1998 | Avery et al. |
| 5,743,274 A | 4/1998 | Peyman |
| 5,766,242 A | 6/1998 | Wong et al. |
| 5,766,619 A | 6/1998 | Aiache et al. |
| 5,770,592 A | 6/1998 | Clark |
| 5,773,019 A | 6/1998 | Ashton et al. |
| 5,797,898 A | 8/1998 | Santini, Jr. et al. |
| 5,824,072 A | 10/1998 | Wong |
| 5,824,073 A | 10/1998 | Peyman |
| 5,830,173 A | 11/1998 | Avery et al. |
| 5,836,935 A | 11/1998 | Ashton et al. |
| 5,902,598 A | 5/1999 | Chen et al. |
| 5,904,144 A | 5/1999 | Hammang et al. |
| 5,916,584 A | 6/1999 | O'Donoghue |
| 6,001,386 A | 12/1999 | Ashton et al. |
| 6,074,661 A | 6/2000 | Olejnik et al. |
| 6,110,485 A | 8/2000 | Olejnik |
| 6,120,460 A | 9/2000 | Abreu |
| 6,126,687 A | 10/2000 | Peyman |
| 6,146,366 A | 11/2000 | Schachar |
| 6,217,895 B1 | 4/2001 | Guo et al. |
| 6,375,972 B1 | 4/2002 | Guo et al. |
| 6,378,526 B1 | 4/2002 | Bowman et al. |
| 6,397,849 B1 | 6/2002 | Bowman et al. |
| 6,413,245 B1 | 7/2002 | Yaacobi et al. |
| 6,413,540 B1 | 7/2002 | Yaacobi |
| 6,416,777 B1 | 7/2002 | Yaacobi |
| 6,669,950 B1 | 12/2003 | Yaacobi |
| 6,713,081 B1 | 3/2004 | Robinson et al. |
| 6,719,750 B1 | 4/2004 | Varner et al. |
| 2002/0188282 A1 | 12/2002 | Greenberg |
| 2003/0175324 A1 | 9/2003 | Robinson et al. |
| 2004/0180075 A1 | 9/2004 | Robinson et al. |
| 2004/0219181 A1 | 11/2004 | Viscasillas |

FOREIGN PATENT DOCUMENTS

| | | |
|---|---|---|
| EP | 0 904 787 | 3/1999 |
| RU | 2149615 | 5/2000 |
| WO | WO 94/05257 | 3/1994 |
| WO | WO 95/26734 | 10/1995 |
| WO | WO 95/28984 | 11/1995 |
| WO | WO 96/36377 | 11/1996 |
| WO | WO 97/14415 | 4/1997 |
| WO | WO 98/23228 | 6/1998 |
| WO | WO 98/43611 | 10/1998 |
| WO | WO 99/07418 | 2/1999 |
| WO | WO 99/11244 | 3/1999 |
| WO | WO 99/32104 | 7/1999 |
| WO | WO 99/45920 | 9/1999 |
| WO | WO 00/56340 | 3/2000 |
| WO | WO 00/37066 | 6/2000 |
| WO | WO 01/49226 | 7/2001 |
| WO | WO 02/100318 | 2/2002 |

OTHER PUBLICATIONS

"Method of Placing Irrigation System into Tenon's Space," E.I. Sidorenko, et al., Abstract of Russian Patent No. RU 2123314, issued Dec. 20, 1998, 1 pg.

"A New method for Posterior Sub-Tenon's Drug Administration," Nesterov, et al., Ophthalmic Surgery, vol. 24, No. 1, Jan. 1993, pp. 59-61.

DIALOG File 266:FEDRIP database record; Identifyiing No. 122098; "Implantation of a Sub-Tenon Drug Delivery Device Loaded with a Test Article in Rabbits and Distribution of the Test Article in Ocular Tissues;" Compiled and distributed by NTIS; 1 page; Jun. 3, 1999.

DIALOG File 266: FEDRIP database record; Identifying No. 134284; "Implantation of a Sub-Tenon Drug Delivery Device Loaded with a Test Article in Rabbits and Distribution of the Test Article in Ocular Tissues;"Complied and distributed by NTIS; 1 page.

DIALOG File 266: FEDRIP database record; Identifying No. 131476: Ocular Bioavailability of AL-3789 and AL-4940 after Sub-Tenon's Injection of AL-3789 Ophthalmic Suspensions in New Zealand White Rabbits; Complied and distributed by NTIS; 1 page.

* cited by examiner

OPHTHALMIC DRUG DELIVERY DEVICE

This application is a continuation of PCT/US02/23048 filed Jul. 22, 2002 entitled "Ophthalmic Drug Delivery Device," which claims priority from U.S. Provisional Application No. 60/307,284 filed Jul. 23, 2001. This application is related to U.S. Pat. Nos. 6,413,540 and 6,416,777, both of which are incorporated herein in their entirety by this reference.

FIELD OF THE INVENTION

The present invention generally pertains to biocompatible implants for delivery of pharmaceutically active agents to the eye. More particularly, but not by way of limitation, the present invention pertains to biocompatible implants for delivery of pharmaceutically active agents to the posterior segment of the eye.

DESCRIPTION OF THE RELATED ART

Several diseases and conditions of the posterior segment of the eye threaten vision. Age related macular degeneration (ARMD), choroidal neovascularization (CNV), retinopathies (e.g., diabetic retinopathy, vitreoretinopathy), retinitis (e.g., cytomegalovirus (CMV) retinitis), uveitis, macular edema, glaucoma, and neuropathies are several examples.

Age related macular degeneration (ARMD) is the leading cause of blindness in the elderly. ARMD attacks the center of vision and blurs it, making reading, driving, and other detailed tasks difficult or impossible. About 200,000 new cases of ARMD occur each year in the United States alone. Current estimates reveal that approximately forty percent of the population over age 75, and approximately twenty percent of the population over age 60, suffer from some degree of macular degeneration. "Wet" ARMD is the type of ARMD that most often causes blindness. In wet ARMD, newly formed choroidal blood vessels (choroidal neovascularization (CNV)) leak fluid and cause progressive damage to the retina.

In the particular case of CNV in ARMD, three main methods of treatment are currently being developed, (a) photocoagulation, (b) the use of angiogenesis inhibitors, and (c) photodynamic therapy. Photocoagulation is the most common treatment modality for CNV. However, photocoagulation can be harmful to the retina and is impractical when the CNV is near the fovea. Furthermore, over time, photocoagulation often results in recurrent CNV. Oral or parenteral (non-ocular) administration of anti-angiogenic compounds is also being tested as a systemic treatment for ARMD. However, due to drug-specific metabolic restrictions, systemic administration usually provides sub-therapeutic drug levels to the eye. Therefore, to achieve effective intraocular drug concentrations, either an unacceptably high dose or repetitive conventional doses are required. Periocular injections of these compounds often result in the drug being quickly washed out and depleted from the eye, via periocular vasculature and soft tissue, into the general circulation. Repetitive sub-Tenon's capsule injections of these compounds carry the potential risk of penetrating the globe and the severe, often blinding, complications of retinal detachment and endophthalmitis. In addition, it is difficult to perform such injections in a reproduceable manner, and each injection may result in a different distribution of drug along the scleral surface. Furthermore, many attempts to inject drug below the Tenon's capsule actually result in injections into the Tenon's capsule itself or the surrounding tissue, which is not desirable. Repetitive intraocular injections may also result in retinal detachment and endophthalmitis. Photodynamic therapy is a new technology for which the long-term efficacy is still largely unknown.

In order to prevent complications related to the above-described treatments and to provide better ocular treatment, researchers have suggested various implants aimed at delivery of anti-angiogenic compounds to the eye. U.S. Pat. No. 5,824,072 to Wong discloses a non-biodegradable polymeric implant with a pharmaceutically active agent disposed therein. The pharmaceutically active agent diffuses through the polymer body of the implant into the target tissue. The pharmaceutically active agent may include drugs for the treatment of macular degeneration and diabetic retinopathy. The implant is placed substantially within the tear fluid upon the outer surface of the eye over an avascular region, and may be anchored in the conjunctiva or sclera; episclerally or intrasclerally over an avascular region; substantially within the suprachoroidial space over an avascular region such as the pars plana or a surgically induced avascular region; or in direct communication with the vitreous.

U.S. Pat. No. 5,476,511 to Gwon et al. discloses a polymer implant for placement under the conjunctiva of the eye. The implant may be used to deliver neovascular inhibitors for the treatment of ARMD and drugs for the treatment of retinopathies, and retinitis. The pharmaceutically active agent diffuses through the polymer body of the implant.

U.S. Pat. No. 5,773,019 to Ashton et al. discloses a non-bioerodable polymer implant for delivery of certain drugs including angiostatic steroids and drugs such as cyclosporine for the treatment of uveitis. Once again, the pharmaceutically active agent diffuses through the polymer body of the implant.

All of the above-described implants require careful design and manufacture to permit controlled diffusion of the pharmaceutically active agent through a polymer body or polymer membrane to the desired site of therapy. Drug release from these devices depends on the porosity and diffusion characteristics of the matrix or membrane, respectively. These parameters must be tailored for each drug moiety to be used with these devices. Consequently, these requirements generally increase the complexity and cost of such implants.

U.S. Pat. No. 5,824,073 to Peyman discloses an indentor for positioning in the eye. The indentor has a raised portion that is used to indent or apply pressure to the sclera over the macular area of the eye. This patent discloses that such pressure decreases choroidal congestion and blood flow through the subretinal neovascular membrane, which, in turn, decreases bleeding and subretinal fluid accumulation.

U.S. Pat. Nos. 5,725,493 and 5,830,173 both disclose non-bioerodable implants that have a drug containing reservoir located outside the globe of the eye and a drug delivery tube running from the reservoir and into the vitreous cavity at the pars plana.

Despite the above-described ophthalmic implants, a need still exists for a surgically implantable ophthalmic drug delivery device capable of safe, effective, rate-controlled, delivery of a wide variety of pharmaceutically active agents. The surgical procedure for implanting such a device should be safe, simple, quick, and capable of being performed in an outpatient setting. Ideally, such a device should be easy and economical to manufacture. Furthermore, because of its versatility and capability to deliver a wide variety of pharmaceutically active agents, such an implant should be capable of use in ophthalmic clinical studies to deliver various agents that create a specific physical condition in a patient. Ideally, such an ophthalmic drug delivery device would be capable of localized delivery of pharmaceutically active agents to a specific portion of the retina, as well as pan-retinal delivery of pharmaceutically active agents.

SUMMARY OF THE INVENTION

One aspect of the present invention is an ophthalmic drug delivery device having a first end and a second end, an injection port, a reservoir, and a sleeve. The injection port is for sealingly engaging a needle of a syringe, which is for providing a fluid comprising a pharmaceutically active agent. The reservoir is disposed within the device, is fluidly coupled to the injection port, and has an opening for communicating the fluid to an outer surface of a sclera of an eye. The sleeve is for engaging the device proximate overlapping portions of the first end and the second end for forming a generally ring-shaped three-dimensional geometry upon implantation of the device on the outer surface of the sclera.

BRIEF DESCRIPTION OF THE DRAWINGS

For a more complete understanding of the present invention, and for further objects and advantages thereof, reference is made to the following description taken in conjunction with the accompanying drawings in which.

DETAILED DESCRIPTION OF THE PREFERRED EMBODIMENTS

The preferred embodiments of the present invention and their advantages are best understood by referring to FIGS. 1–4 of the drawings, like numerals being used for like and corresponding parts of the various drawings.

FIGS. 1–4 schematically illustrate an ophthalmic drug delivery device 10 according to a preferred embodiment of the present invention. Device 10 may be used in any case where delivery of a pharmaceutically active agent to the eye is required. Device 10 is particularly useful for delivery of active agents to the posterior segment of the eye. A preferred use for device 10 is the delivery of pharmaceutically active agents to the retina for treating ARMD, choroidial neovascularization (CNV), retinopathies, retinitis, uveitis, macular edema, and glaucoma.

Figure 1:
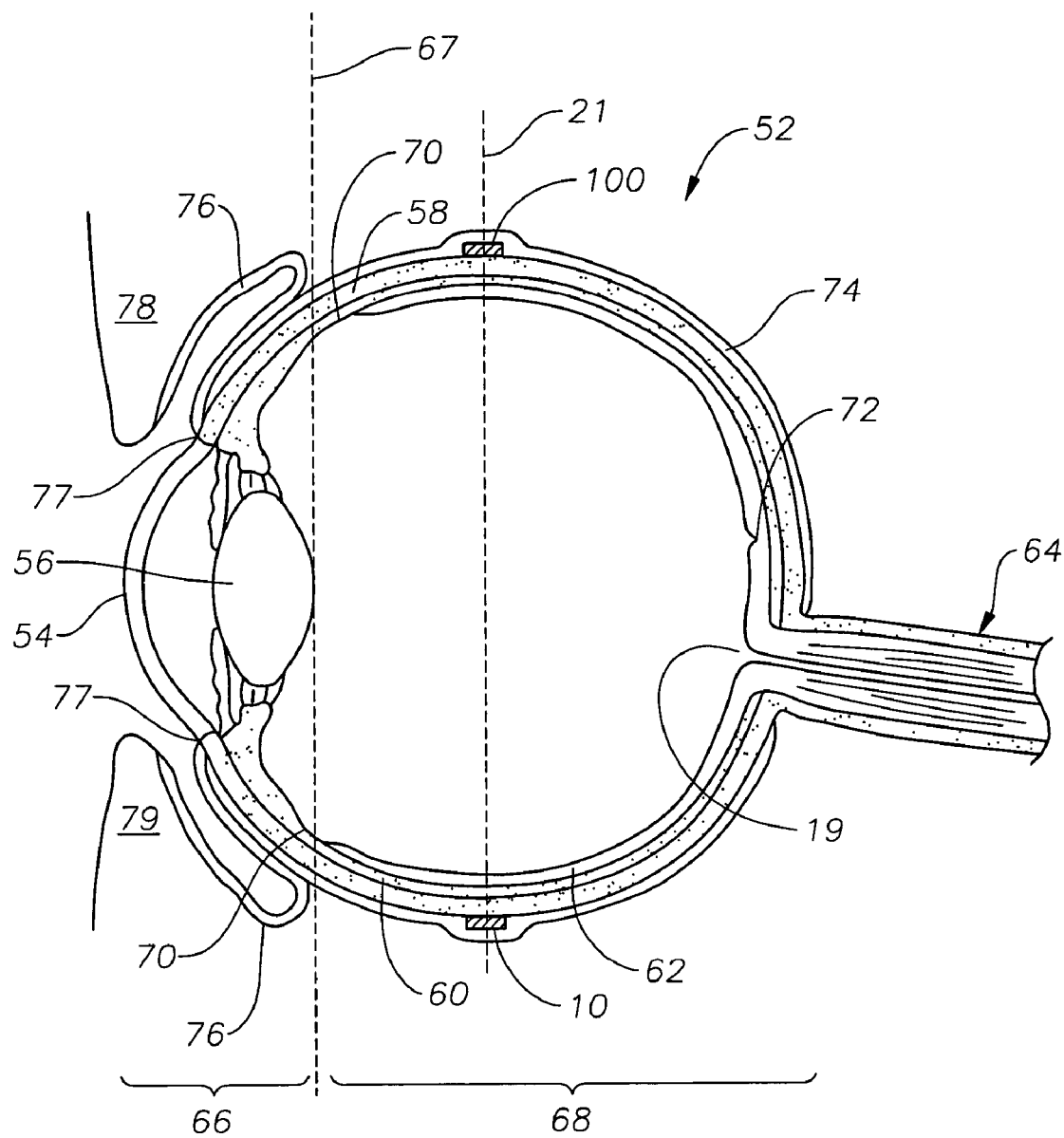
FIG. 1 is a side sectional view schematically illustrating the human eye.
Figure 2:
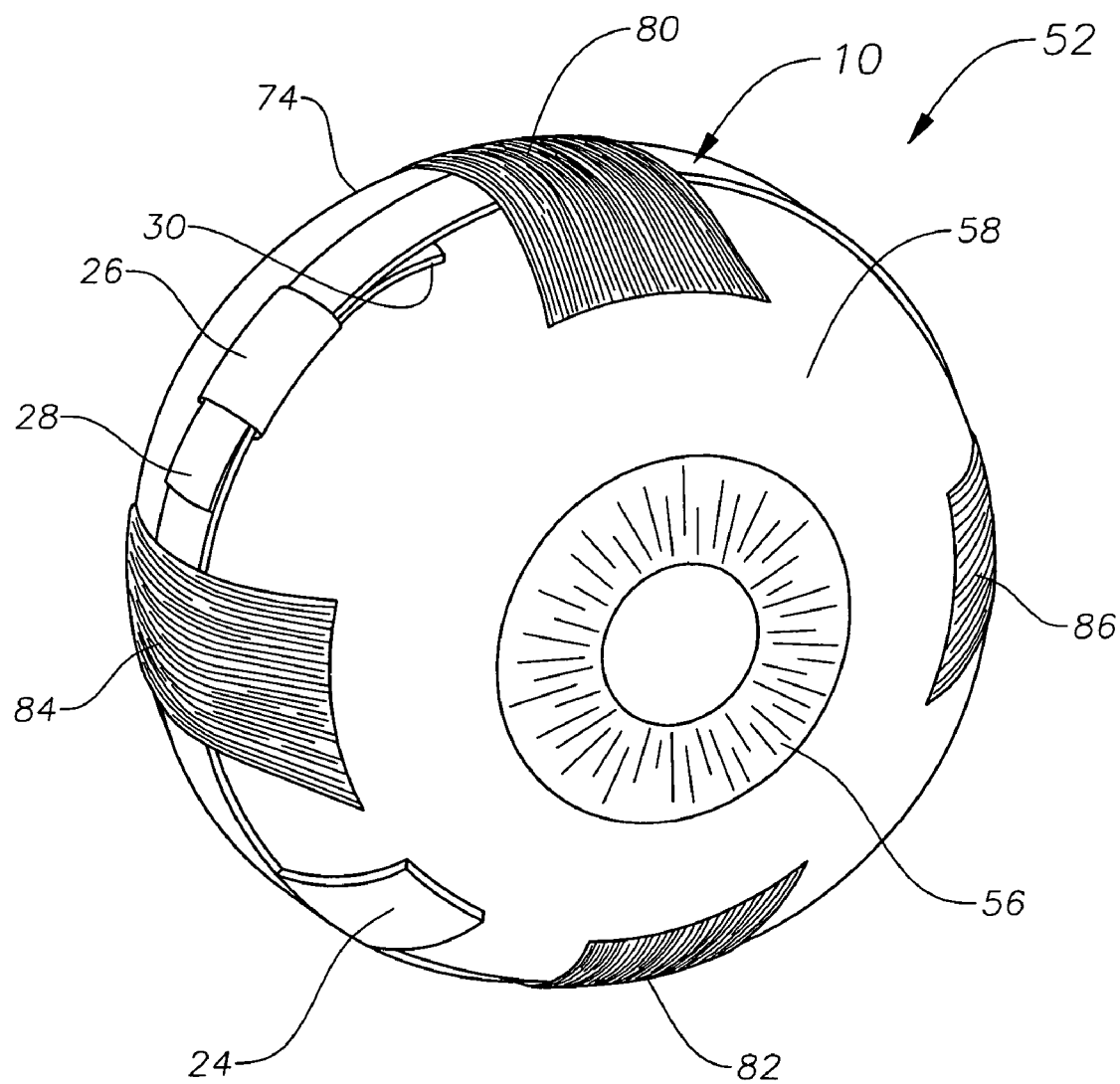
FIG. 2 is a partially dissected, three dimensional schematic representation of the human eye.

Referring to FIGS. 1–2, a human eye 52 is schematically illustrated. Eye 52 has a cornea 54, a lens 56, a sclera 58, a choroid 60, a retina 62, and an optic nerve 64. An anterior segment 66 of eye 52 generally includes the portions of eye 52 anterior of a line 67. A posterior segment 68 of eye 52 generally includes the portions of eye 52 posterior of line 67. Retina 62 is physically attached to choroid 60 in a circumferential manner proximate pars plana 70. Retina 62 has a macula 72 located slightly lateral to its optic disk 19. As is well known in the ophthalmic art, macula 72 is comprised primarily of retinal cones and is the region of maximum visual acuity in retina 62. A Tenon's capsule or Tenon's membrane 74 is disposed on sclera 58. A conjunctiva 76 covers a short area of the globe of eye 52 posterior to limbus 77 (the bulbar conjunctiva) and folds up (the upper cul-de-sac) or down (the lower cul-de-sac) to cover the inner areas of upper eyelid 78 and lower eyelid 79, respectively. Conjunctiva 76 is disposed on top of Tenon's capsule 74. Eye 52 also has an equator 21. As shown in FIG. 2, superior rectus muscle 80, inferior rectus muscle 82, lateral rectus muscle, 84, and medial rectus muscle 86 are attached to sclera 58.

As is shown in FIGS. 1 and 2, and as is described in greater detail hereinbelow, device 10 is preferably disposed directly on the outer surface of sclera 58, below Tenon's capsule 74 for treatment of most posterior segment diseases or conditions. Device 10 is most preferably disposed directly on the outer surface of sclera 58, below Tenon's capsule 74, proximate equator 21.

Figure 3:
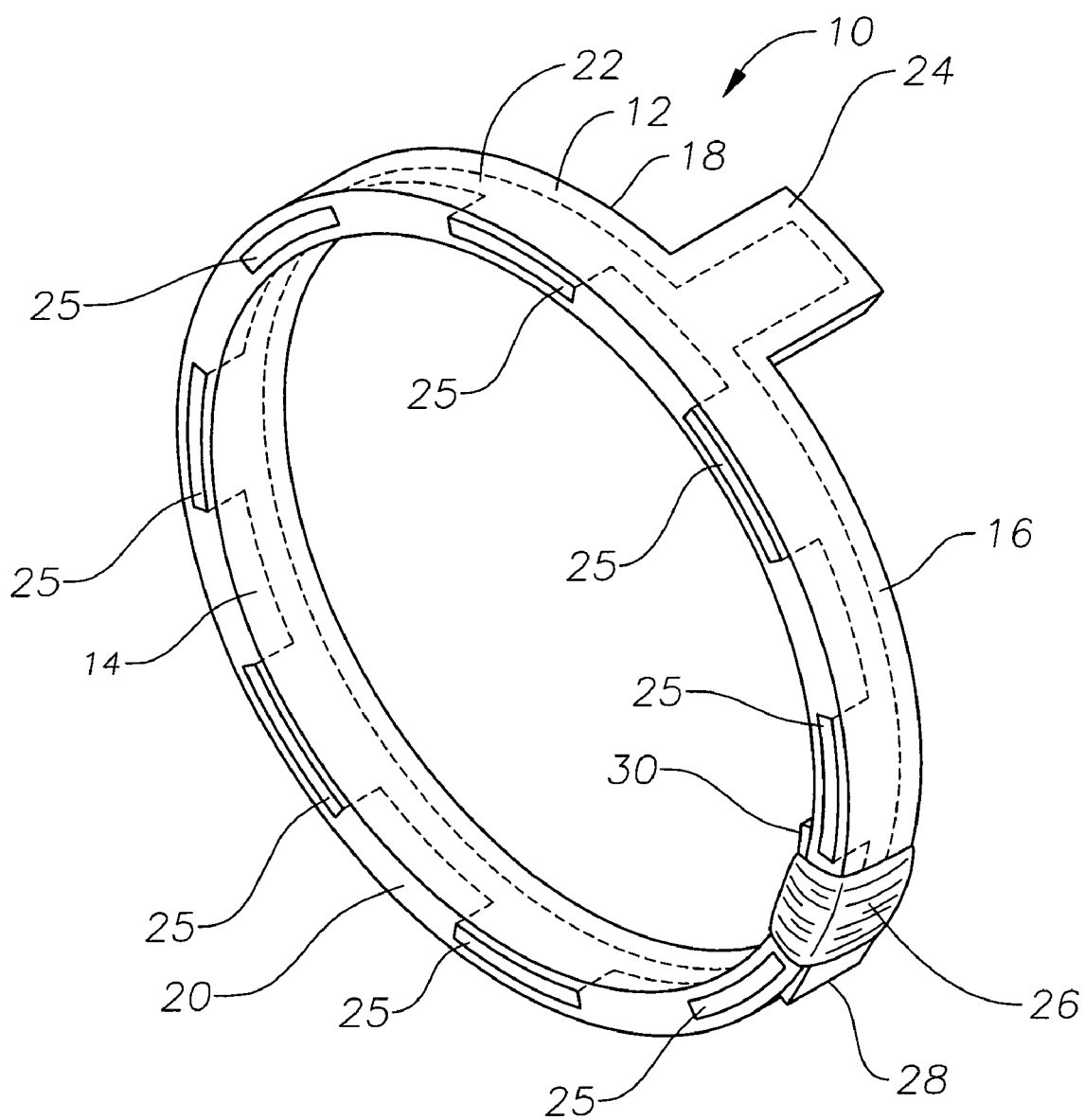
FIG. 3 is a perspective view of an ophthalmic drug delivery device according to a preferred embodiment of the present invention.
Figure 4:
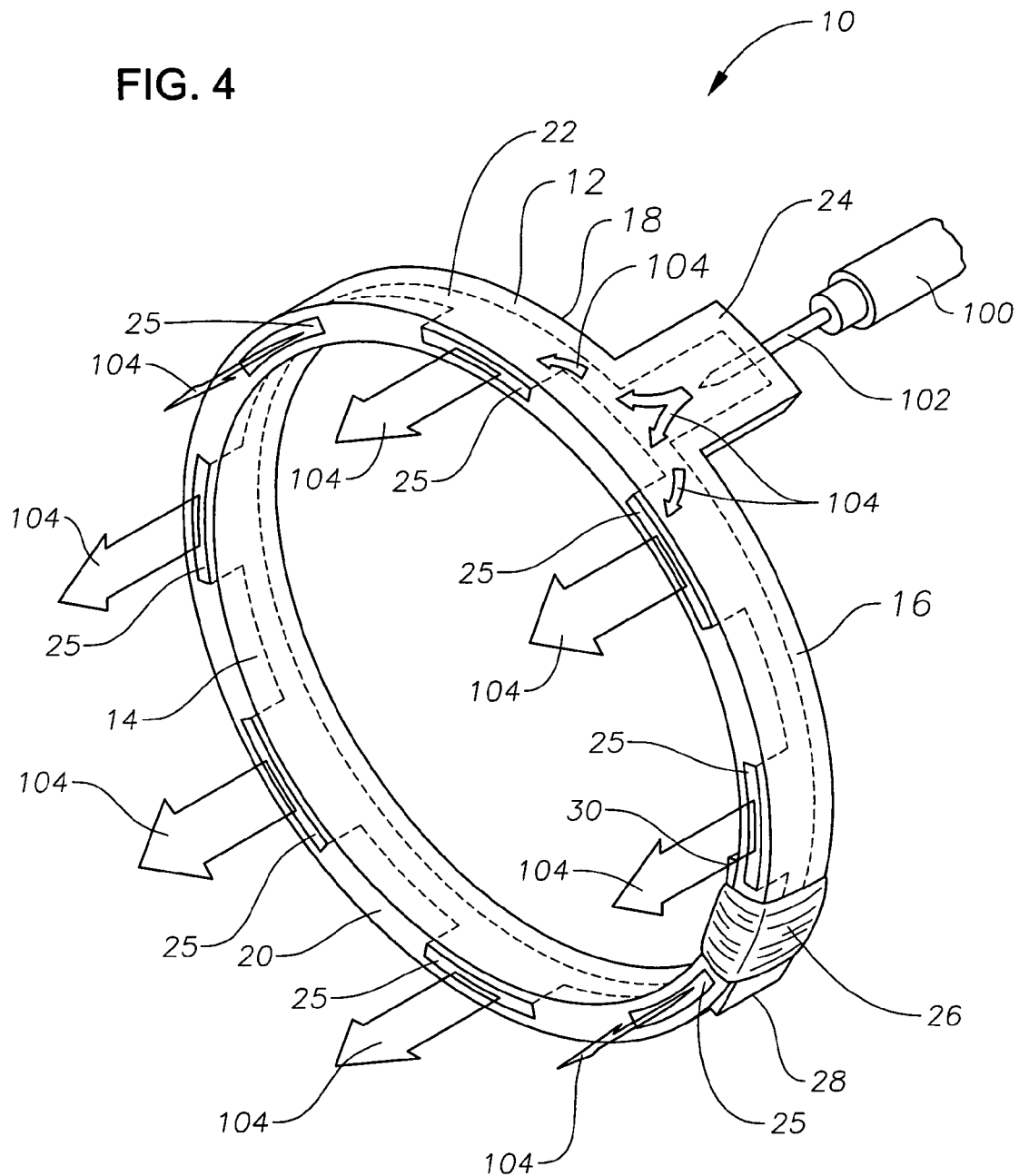
FIG. 4 is a perspective view of the ophthalmic drug delivery device of FIG. 3 showing a preferred method of operation.

FIGS. 3 and 4 schematically illustrate device 10 in greater detail. Device 10 preferably includes a body 12 having a generally ring-shaped three-dimensional geometry in its assembled state shown in FIGS. 3 and 4. In its unassembled stated, body 12 preferably has a generally rectangular three-dimensional geometry. A sleeve 26 encircles overlapping ends 28 and 30 of body 12 to maintain the ring-shaped three-dimensional geometry.

Body 12 has a scleral surface 14, an orbital surface 16, an anterior side 18, and a posterior side 20. Body 12 also has a reservoir 22 located in its interior. Reservoir 22 preferably runs the entire length of body 80, and preferably has a plurality of openings 25 to posterior side 20. Although not shown in FIGS. 3–4, reservoir 22 may also have one or more openings to scleral surface 14, anterior side 18, or orbital surface 16 of body 12. As shown in FIGS. 3–4, openings 25 have a generally rectangular cross-section, but any cross-section can be used for these openings.

Body 12 preferably further has an injection port 24. At least a portion of injection port 24 is preferably made of a fluid impervious material that can be penetrated by a needle and that reseals itself upon removal of the needle. A preferred material is silicone rubber. In addition, injection port 24 is preferably colored or marked by raised protuberances. Injection port 24 preferably extends from anterior side 18 of body 12. Reservoir 22 extends into injection port 24.

The remainder of body 12 preferably comprises a biocompatible, non-bioerodable material. Body 12 more preferably comprises a biocompatible, non-bioerodable polymeric composition. Said polymeric composition may be a homopolymer, a copolymer, straight, branched, cross-linked, or a blend. Examples of polymers suitable for use in said polymeric composition include silicone, polyvinyl alcohol, ethylene vinyl acetate, polylactic acid, nylon, polypropylene, polycarbonate, cellulose, cellulose acetate, polyglycolic acid, polylactic-glycolic acid, cellulose esters, polyethersulfone, acrylics, their derivatives, and combinations thereof. Examples of suitable soft acrylics are more fully disclosed in U.S. Pat. No. 5,403,901, which is incorporated herein in its entirety by reference. Said polymeric composition most preferably comprises silicone. Of course, said polymeric composition may also comprise other conventional materials that affect its physical properties, including, but not limited to, porosity, tortuosity, permeability, rigidity, hardness, and smoothness. Exemplary materials affecting certain ones of these physical properties include conventional plasticizers, fillers, and lubricants. Said polymeric composition may comprise other conventional materials that affect its chemical properties, including, but not limited to, toxicity and hydrophobicity.

As shown in FIG. 4, a conventional syringe 100 and needle 102 may be used to impart a fluid 104 (indicated by arrows) containing a pharmaceutically active agent or agents into reservoir 22 via injection port 24. Fluid 104 may comprise a solution, a suspension, an emulsion, an ointment, a gel forming solution, a gel, a bioerodable polymer, a non-bioerodable polymer, microparticles, or combinations thereof. Most preferably, fluid 104 is a suspension with or without microparticles formed from bioerodable polymers. Fluid 104 includes one or more ophthalmically acceptable pharmaceutically active agents, and may also include conventional non-active incipients. Examples of pharmaceutically active agents suitable for fluid 104 are anti-infectives, including, without limitation, antibiotics, antivirals, and antifungals; antiallergenic agents and mast cell stabilizers; steroidal and non-steroidal anti-inflammatory agents; cyclooxygenase inhibitors, including, without limitation, Cox I and Cox II inhibitors; combinations of anti-infective and anti-inflammatory agents; decongestants; anti-glaucoma agents, including, without limitation, adrenergics, β-adrenergic blocking agents, α-adrenergic agonists, parasypathomimetic agents, cholinesterase inhibitors, carbonic anhydrase inhibitors, and prostaglandins; combinations of anti-glaucoma agents; antioxidants; nutritional supplements; drugs for the treatment of cystoid macular edema including, without limitation, non-steroidal anti-inflammatory agents; drugs for the treatment of ARMD, including, without limitation, angiogenesis inhibitors and nutritional supplements; drugs for the treatment of herpetic infections and CMV ocular infections; drugs for the treatment of proliferative vitreoretinopathy including, without limitation, antimetabolites and fibrinolytics; wound modulating agents, including, without limitation, growth factors; antimetabolites; neuroprotective drugs, including, without limitation, eliprodil; and angiostatic steroids for the treatment of diseases or conditions of posterior segment 26, including, without limitation, ARMD, CNV, retinopathies, retinitis, uveitis, macular edema, and glaucoma. Such angiostatic steroids are more fully disclosed in U.S. Pat. Nos. 5,679,666 and 5,770,592. Preferred ones of such angiostatic steroids include 4,9(11)-Pregnadien-17α,21-diol-3,20-dione and 4,9(11)-Pregnadien-17α,21-diol-3,20-dione-21-acetate. These preferred angiostatic steroids are preferably formulated as a suspension. A preferred non-steroidal anti-inflammatory for the treatment of cystoid macular edema is nepafenac. The conventional non-active excipients may include, but are not limited to, ingredients to enhance the stability, solubility, penetrability, or other properties of fluid 104. In particular, hydrolytic enzymes such as proteases, esterases, hyaluronidases, and collegenases may be utilized to enhance the penetration of the pharmaceutically active agents through natural and newly formed connective tissue that may encapsulate device 10 after implantation. Body 12 is preferably impermeable to fluid 104.

Device 10 may be made by conventional polymer processing methods, including, but not limited to, injection molding, extrusion molding, transfer molding, and compression molding. Preferably, device 10 is formed using conventional injection molding techniques.

Device 10 is preferably surgically placed directly on the outer surface of sclera 58 below Tenon's capsule 74 using a simple surgical technique that is capable of being performed in an outpatient setting. The surgeon first performs a 360 degree peritomy about 3 mm posterior to limbs 77 of eye 52. The surgeon then performs a blunt dissection to separate Tenon's capsule 74 from sclera 58 up to a point slightly posterior of equator 21. As shown best in FIG. 2, the surgeon then positions device 10 on the outer surface of sclera 58 below superior rectus muscle 80, medial rectus muscle 86, inferior rectus muscle 82, and lateral rectus muscle 84 generally near equator 21. Injection port 24 is preferably located in the infra-temporal quadrant of eye 52 between inferior rectus muscle 82 and lateral rectus muscle 84. The surgeon tightens device 10 around sclera 58 and fixes overlapping ends 28 and 30 of body 12 with sleeve 26. The surgeon then moves Tenon's capsule 74 back to its original position and sutures it in place. After closing, the surgeon places antibiotic ointment on the surgical wound.

Once device 10 is located in the desired position, the surgeon uses syringe 100 and needle 102 to inject fluid 104 into reservoir 22. The surgeon preferably moves lower eyelid 79 downward and instructs the patient to look upward so as to expose injection port 24. Injection port 24 may be easily visualized beneath the Tenon's capsule and any connective tissue encapsulating device 10 due to its color or raised protuberances. The surgeon sticks needle 102 into injection port 24, injects fluid 104 into reservoir 22, and removes needle 102 from the port 24. Port 24 reseals automatically upon removal of the needle. Fluid 104 is disposed throughout reservoir 22, and is in communication with sclera 58 via openings 25, or any other openings from reservoir 22.

It is believed that device 10 can be used to deliver a pharmaceutically effective amount of a pharmaceutically active agent through sclera 58 and choroid 60 into retina 62 for many years, depending on the particular physicochemical properties of the particular fluid 104 and its pharmaceutically active agent employed. Important physicochemical properties include hydrophobicity, solubility, dissolution rate, diffusion coefficient, and tissue affinity. In addition, it is believed that device 10 may be used to deliver both a localized distribution of drug primarily proximate macula 72, or to deliver drug to substantially the entire retina, depending upon the particular fluid 104 and its pharmaceutically active agents and incipients. After reservoir 22 no longer contains any fluid 104, a surgeon may refill reservoir 22 as described hereinabove. Although not shown in FIGS. 1–4, posterior side 20 of body 12 may also include a sharp surface or edge. During refilling of reservoir 22, the surgeon may move device 10 slightly posteriorly so that such sharp surface or edge pierces any connective tissue that may encapsulate device 10 after implantation. Piercing this connective tissue facilitates proper distribution of fluid 104 via openings 25. In addition, unlike repetitive sub-Tenon's capsule injections of drug formulations, device 10 minimizes the risk of penetrating the globe of the eye, always results in fluid 212 being distributed below the Tenon's capsule 74 on the outer surface of sclera 58, and results in a reproduceable distribution of fluid 212 on a desired portion of the outer surface of the sclera 58.

From the above, it may be appreciated that the present invention provides improved devices and methods for safe, effective, rate-controlled delivery of a variety of pharmaceutically active agents to the eye. The devices of the present invention are especially useful for localized and/or pan-retinal delivery of pharmaceutically active agents to the posterior segment of the eye to combat diseases such as ARMD, CNV, retinopathies, retinitis, uveitis, macular edema, and glaucoma. The surgical procedure for implanting the devices is safe, simple, quick, and capable of being performed in an outpatient setting. The devices are easy and economical to manufacture. Furthermore, because of their capability to deliver a wide variety of pharmaceutically active agents, such devices are useful in clinical studies to deliver various agents that create a specific physical condition in a patient or animal subject.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. An ophthalmic drug delivery device, comprising:
   a first end and a second end;
   an injection port for sealingly engaging a needle of a syringe, said syringe for providing a fluid comprising a pharmaceutically active agent;
   a reservoir disposed within said device, fluidly coupled to said injection port, and having an opening for communicating said fluid to an outer surface of a sclera of an eye; and
   a sleeve for engaging said device proximate overlapping portions of said first end and said second end for forming a generally ring-shaped three-dimensional geometry upon implantation of said device on said outer surface of said sclera.

2. The ophthalmic drug delivery device of claim 1 further comprising an anterior side, and wherein said injection port is disposed on said anterior side.

3. The ophthalmic drug delivery device of claim 1 further comprising a posterior side, and wherein said posterior side comprises a sharp exterior surface for piercing connective tissue that may encapsulate said device upon implantation on said outer surface of said sclera.

4. The ophthalmic drug delivery device of claim 1 wherein said reservoir comprises a plurality of said openings for communicating said fluid to said outer surface of said sclera.

5. The ophthalmic drug delivery device of claim 1 wherein said device delivers said pharmaceutically active agent through said sclera and a choroid into a retina of said eye.

6. The ophthalmic drug delivery device of claim 5 wherein said device delivers said pharmaceutically active agent to substantially all of said retina.

7. The ophthalmic drug delivery device of claim 5 wherein said device delivers said pharmaceutically active agent to a portion of said retina proximate said device.

* * * * *